United States Patent
Cohen et al.

(10) Patent No.: US 6,720,556 B2
(45) Date of Patent: Apr. 13, 2004

(54) ELECTRON SPECTROSCOPY EMPLOYING CONTROLLED SURFACE CHARGING

(75) Inventors: Hagai Cohen, Rehovot (IL); Israel Rubinstein, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 190 days.

(21) Appl. No.: 09/847,583

(22) Filed: May 3, 2001

(65) Prior Publication Data

US 2002/0020814 A1 Feb. 21, 2002

(30) Foreign Application Priority Data

Jul. 6, 2000 (IL) .................................................. 137208

(51) Int. Cl.[7] ...................... G01N 23/227; H01J 37/285; H01J 37/26
(52) U.S. Cl. ...................... 250/306; 250/307; 250/305; 250/310; 250/492.2; 250/492.3
(58) Field of Search ................................. 250/305, 306, 250/307, 310, 492.2, 492.3

(56) References Cited

U.S. PATENT DOCUMENTS

| | | | | |
|---|---|---|---|---|
| 5,028,778 A | * | 7/1991 | Ninomiya et al. | 250/305 |
| 5,352,894 A | * | 10/1994 | Yasuo | 250/305 |
| 5,374,318 A | * | 12/1994 | Rabalais et al. | 428/469 |
| 5,408,881 A | * | 4/1995 | Piche et al. | 73/582 |
| 5,432,345 A | * | 7/1995 | Kelly | 250/306 |
| 5,510,481 A | * | 4/1996 | Bednarski et al. | 536/120 |
| 5,656,406 A | * | 8/1997 | Ikuno et al. | 430/67 |
| 5,665,435 A | * | 9/1997 | Smentkowski et al. | 427/551 |
| 5,821,171 A | * | 10/1998 | Hong et al. | 438/767 |
| 5,840,426 A | * | 11/1998 | Smentkowski et al. | 428/408 |
| 5,990,476 A | * | 11/1999 | Larson et al. | 250/251 |
| 6,066,403 A | * | 5/2000 | Sherwood et al. | 428/472.3 |
| 6,255,499 B1 | * | 7/2001 | Kuperman et al. | 549/523 |
| 6,284,213 B1 | * | 9/2001 | Paparatto et al. | 423/403 |
| 6,444,217 B1 | * | 9/2002 | Kwok et al. | 424/423 |
| 2002/0020814 A1 | * | 2/2002 | Cohen et al. | 250/306 |
| 2003/0080291 A1 | * | 5/2003 | Larson et al. | 250/306 |
| 2003/0080292 A1 | * | 5/2003 | Watson et al. | 250/306 |

OTHER PUBLICATIONS

"X-ray Photoelectron Spectroscopy (XPS)", http://www-.phi.com/surfcat/3057 cat.pdf.*
Vallier et al., "Chemical totpgraphy analysis using XPS during plasma etching in Si processing", http://www.phys-.tue.nl/FLTPD/Invited/vallier.pdf.*
"Abnormal Binding Energy and Auger parameters", http://www.uwo.ca/ssw/archives/1998/dec98/0008.html.*

* cited by examiner

*Primary Examiner*—Bruce Anderson
*Assistant Examiner*—Bernard Souw
(74) *Attorney, Agent, or Firm*—Browdy and Neimark, P.L.L.C.

(57) ABSTRACT

A method of examining a sample, including: performing a first spectroscopic analysis of a surface portion of the sample when the sample surface portion is in a first electrical charge state; placing the sample surface portion in a second electrical charge state that is different from the first electrical charge state and performing a second spectroscopic analysis of the surface portion of the sample when the sample surface portion is in the second electrical charge state; and comparing the first spectroscopic analysis result with the second spectroscopic analysis result to obtain at least one of structural and electrical information about the sample.

22 Claims, 8 Drawing Sheets

FIGURE 2A
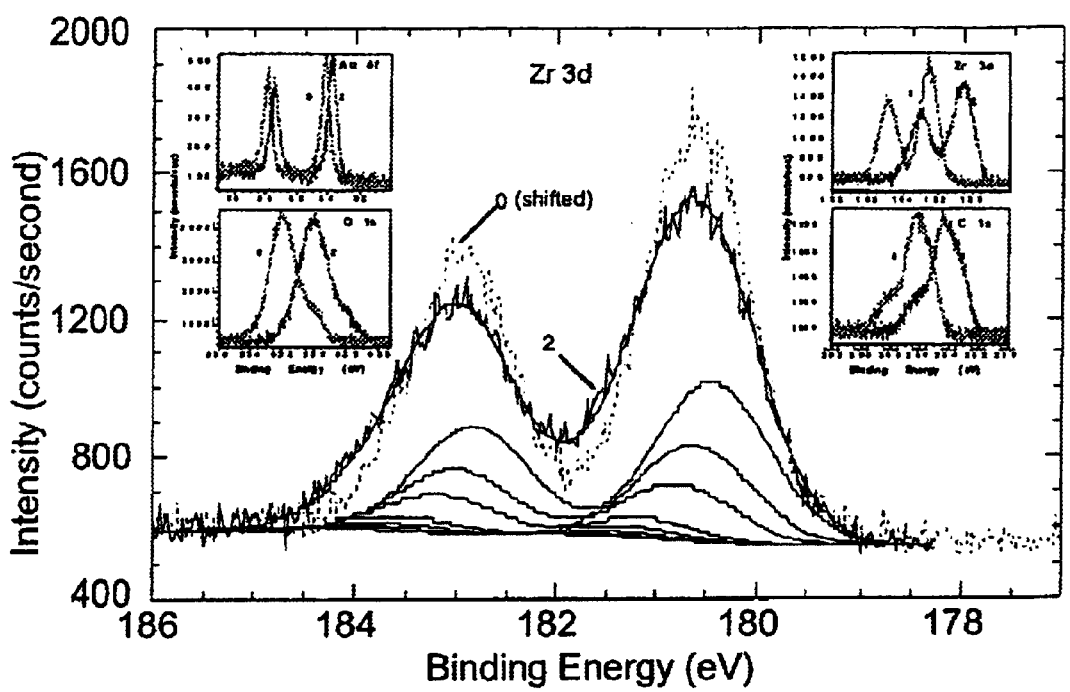
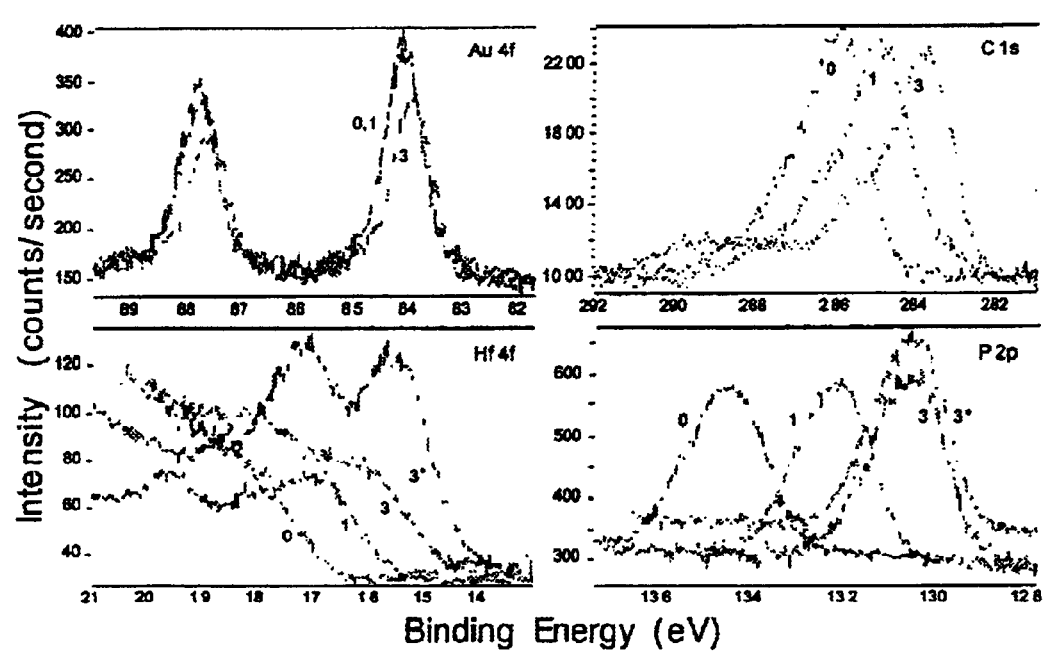
FIGURE 2B

FIGURE 6A
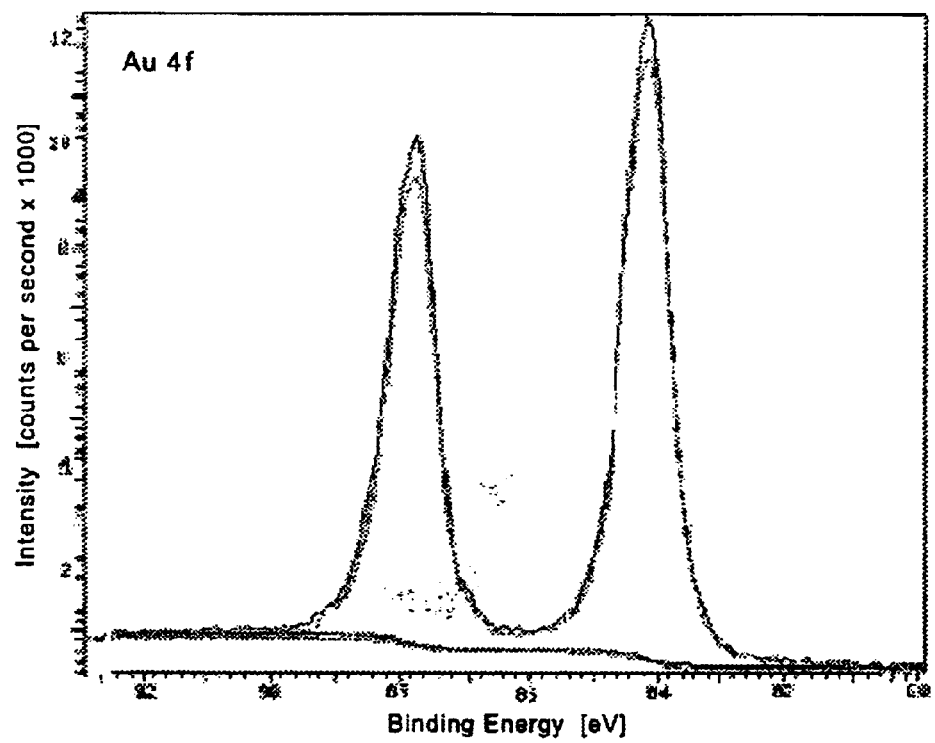
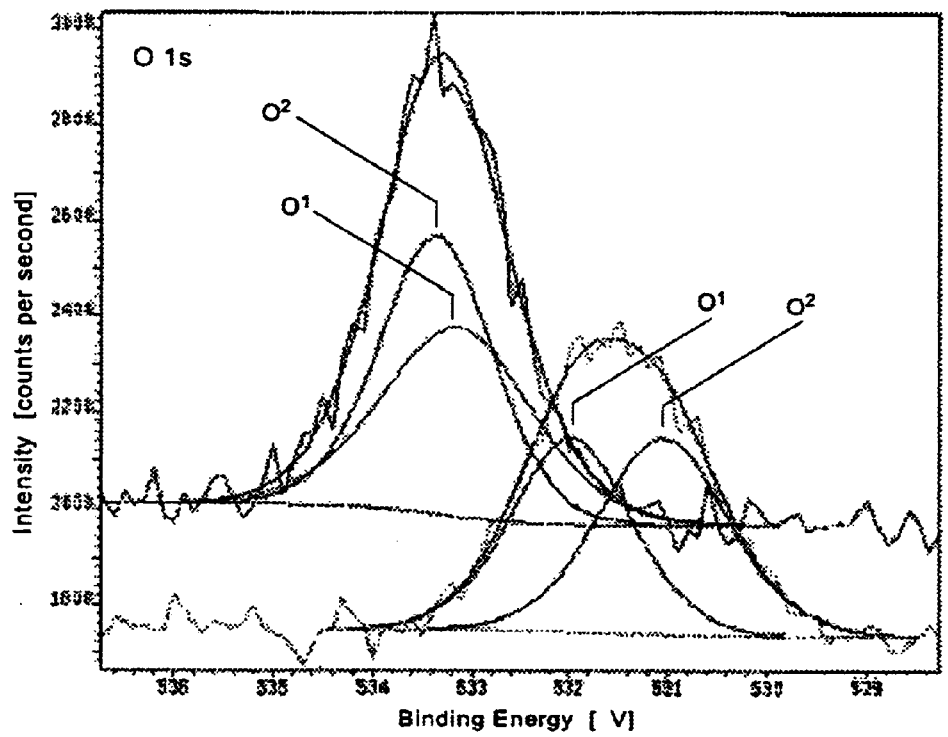
FIGURE 6B

FIGURE 6C
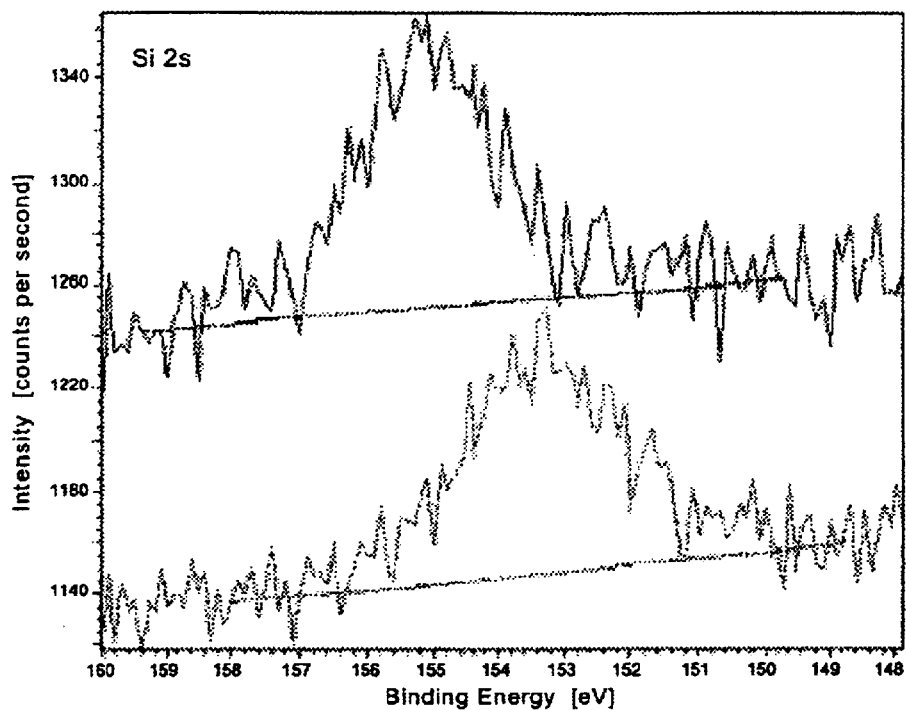
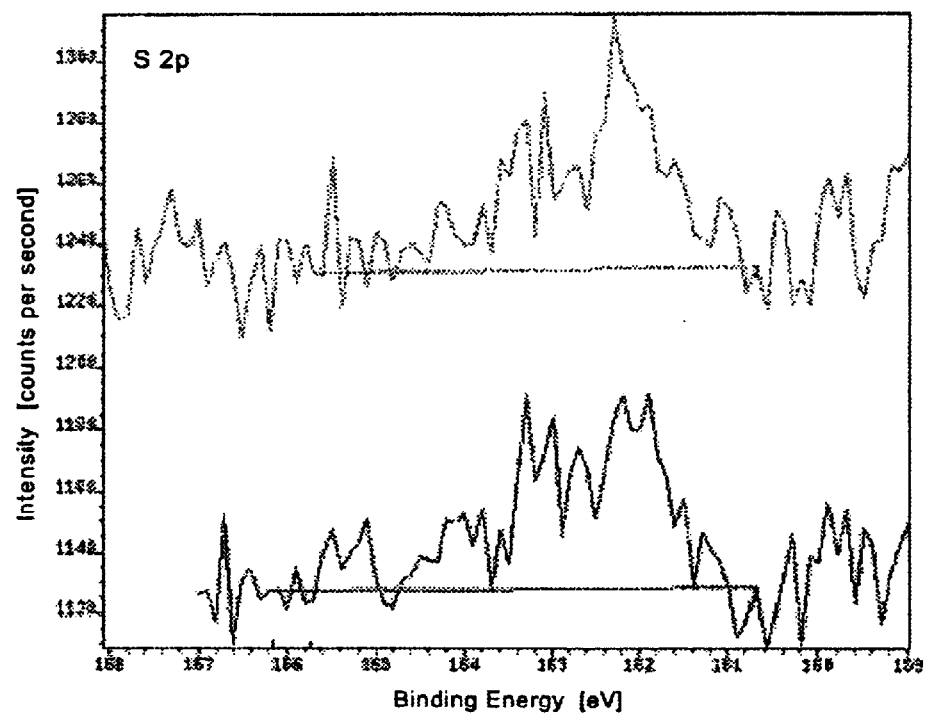
FIGURE 6D

FIGURE 7A
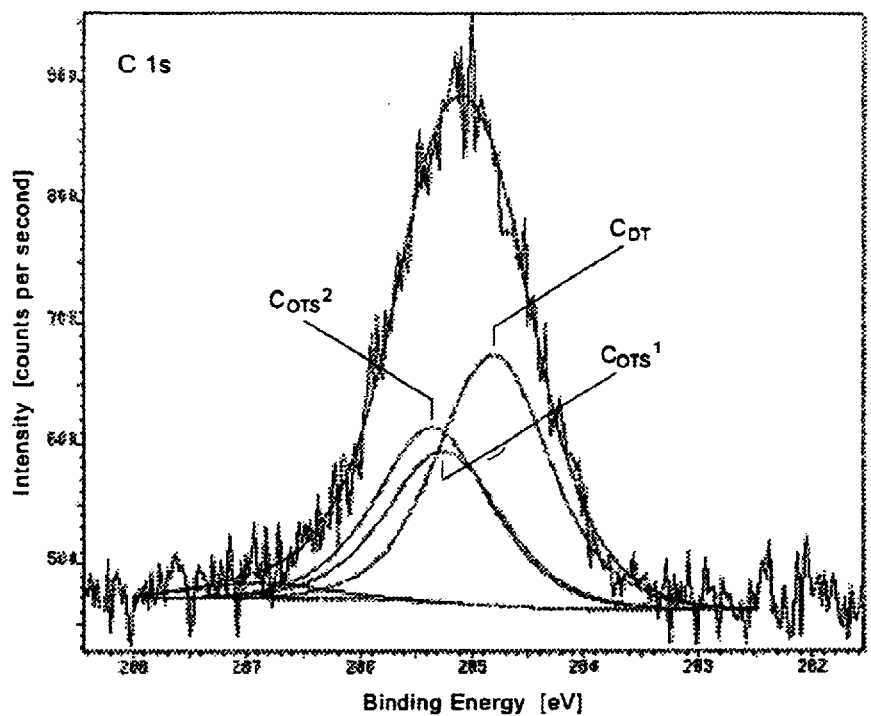
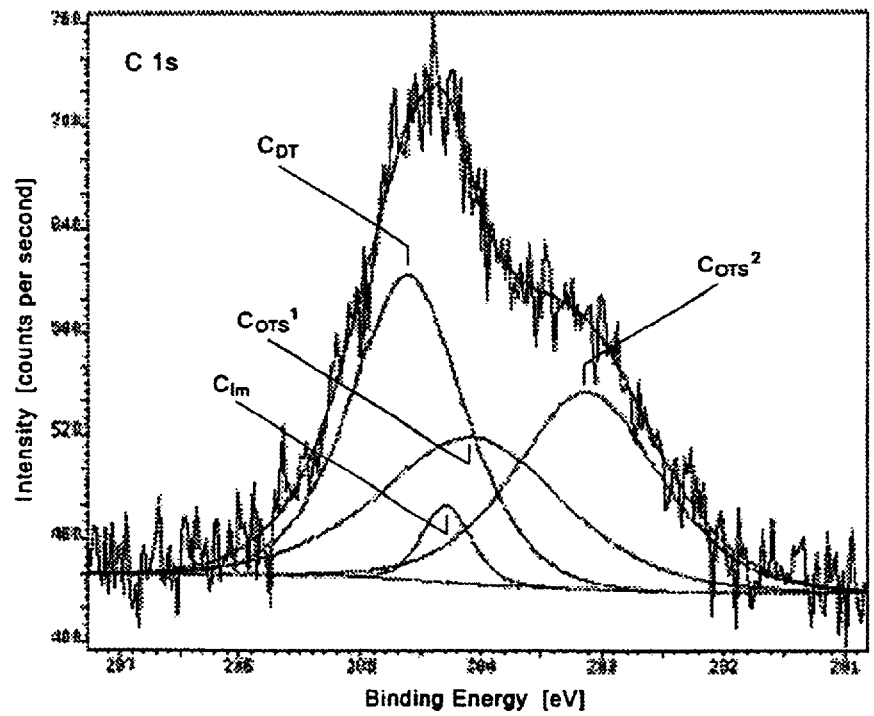
FIGURE 7B ical charging of the sample surface is commonly considered an obstacle to accurate experimental determination of binding energies in XPS measurements of poorly conducting surfaces[6, 19, 20] To compensate the extra positive
ELECTRON SPECTROSCOPY EMPLOYING CONTROLLED SURFACE CHARGING

BACKGROUND OF THE INVENTION

1. Field of the Invention

The present invention relates to the use of electron spectroscopy as a depth profiling or lateral differentiation probe useful, for example, for characterization of optoelectronic devices and other applications of mesoscopic systems, i.e. between the macroscopic solid and the atomic scale.

2. Prior Art

Progress in the development of new microelectronic technologies, leading to smaller, faster and smarter electronic and optoelectronic devices, depends on the ability to construct sophisticated interfacial structures which are well-resolved on the nanometer scale. One of the most acute problems in the development, study and application of such structures is finding characterization techniques suitable for such systems, namely having appropriate resolution in both the lateral and depth directions, the lateral direction being parallel to the surface of a sample at which such structure is disposed and the depth direction being perpendicular to the lateral direction. This is naturally of primary importance in the development stage, but also in the production stage, i.e., for on-line quality control. The continuing decrease in component dimensions, already approaching the nanometer range, poses formidable requirements on characterization methods.

X-ray photoelectron spectroscopy (XPS) is a powerful surface analytical tool, providing superior information on the chemical composition of surfaces and interfacial layers. The technique is based on illumination of the surface with X-rays and analysis of the photoelectrons ejected from the surface, thereby determining the identity and chemical state of atoms located on the surface and up to ca. 10 nm deep. In contrast to its nanometer-scale depth sensitivity, in the lateral direction XPS is essentially a macroscopic technique. Several XPS-based depth profiling methods exist, most prominently those based on ion etching or on analysis of line intensities at different detector angles (angle-resolved XPS). Both suffer from various drawbacks, including induced sample damage, distortions associated with non-planar surfaces, and others. As noted above, in the lateral direction, only macroscopic information is commonly obtained.

In addition, the quest to achieve well-defined features which are resolved on the nanometer length scale and distributed in predetermined patterns on solid surfaces is the heart of future optoelectronic devices and a major goal in science and technology. Structural analysis of such systems usually requires scanning probe methodologies, which are essentially small-area techniques. Large-area analytical tools, such as XPS, are limited in this respect. A fundamental feature of XPS is the contrast between its depth resolution and lateral resolution, typically approaching nm vs. $\mu$m length scales, respectively. This raises serious problems in the study of non-planar or heterogeneous surfaces, it especially when surface variations fall in the region between the two length scales. For various applications, however, this intermediate region is the relevant one; hence, new high resolution—large area characterization methods are crucially needed.

Electrical charging of the sample surface is commonly considered an obstacle to accurate experimental determination of binding energies in XPS measurements of poorly conducting surfaces[6, 19, 20] To compensate the extra positive charge that is a natural consequence of photoelectron emission and stabilize the energy scale on a reasonably correct value, an electron flood gun is routinely used. Such gun creates a generally uniform potential across the studied volume. This, however, is often impossible with structures comprising components which differ in electrical conductivity[9, 21-23] In such cases, chemical information may be smeared due to XPS line shifts that would follow local potential variations. On the other hand, this very effect can be used to gain structural information[10-12]. Several studies[9, 24-26] have focused on various aspects of charging in XPS, indicating that, on a macroscopic scale, differential surface potential can be analyzed using a classical approach based on charge generation vs. discharge rates.[8, 27] Application in surface analysis has been demonstrated.[8, 10, 11,-27-29]

Thin layered structures a few nanometers in thickness impose demanding requirements on the depth sensitivity of analytical methods. X-ray photoelectron spectroscopy (XPS)[1], an effective surface analytical tool providing superior chemical information, offers depth sensitivity inherently appropriate for such nanostructures. However, translation of the XPS integral line intensity into high resolution depth information is not straightforward. The commonly used XPS depth profiling methods, i.e., ion etching[2], angular-resolved XPS (ARXPS)[2], and Tougaard's approach[3], are effective but limited in various aspects[2-5]. Ion etching[2] is inherently destructive and limited in application particularly with soft matter. ARXPS[2], considered nondestructive, is hampered when applied to non-planar morphologies, it requires a large number of measurements (which may induce damage[5]), and is strongly model dependent[4]. Tougaard's approach[3] (quantitative analysis of signal-to-background correlation) requires minimal interference of neighboring lines across a wide spectral range, and is therefore less effective with small signals.

BRIEF SUMMARY OF THE INVENTION

The present invention provides improvements in the observation of such structures by the use of selected controlled surface charging (CSC) in conjunction with electron spectroscopy. CSC is basically non-destructive, allowing fast and convenient data collection. It enables differentiation of spectrally identical atoms at different locations. It is applicable to thicker structures than ARXPS, as the signal is FE not subject to increased attenuation associated with off-normal measurements. The method according to the invention offers several advantages over existing depth profiling techniques and is of general applicability to a large variety of mesoscopic heterostructures. Substrate roughness has only a minor effect on CSC depth profiling. The linear dependence on depth, which occurs in systems that have been studied, is an attractive feature of CSC. However, the invention also offers advantages for the study of other systems that may present more elaborate conduction processes, possibly causing deviations from linearity. Such deviations may contribute to the exploration of additional characteristics of the systems, such as charge distribution, conduction mechanisms, etc.

One embodiment of the invention is a method of examining a sample, comprising: performing a first spectroscopic analysis of a surface portion of the sample when the sample surface portion is in a first electrical charge state; placing the sample surface portion in a second electrical charge state that is different from the first electrical charge state and performing a second spectroscopic analysis of the surface portion of the sample when the sample surface portion is in the second electrical charge state; and comparing the first spectroscopic analysis result with the second spectroscopic analysis result to obtain at least one of structural and electrical information about the sample, wherein the first and second electrical charge states are given values that enable information to be obtained about sample structural features having dimensions of less than 50 nm.

A second embodiment of the invention is a method of examining a sample, comprising: performing a first spectroscopic analysis of a surface portion of the sample when the sample surface portion is in a first electrical charge state; placing the sample surface portion in a second electrical charge state that is different from the first electrical charge state and performing a second spectroscopic analysis of the surface portion of the sample when the sample surface portion is in the second electrical charge state; and comparing the first spectroscopic analysis result with the second spectroscopic analysis result to obtain at least one of structural and electrical information about the sample, wherein each spectroscopic analysis result contains data identifying a characteristic of the spectral response for each of at least two elements contained in the sample, and the step of comparing includes: determining, for each of the at least two elements contained in the sample, a difference between the first spectroscopic analysis result and the second spectroscopic analysis result; and correlating the differences determined in the determining step for the at least two elements to provide a quantitative value of a characteristic of the sample. More specifically, the correlation is between the difference associated with one of the elements and that associated with the other of the elements.

One embodiment of apparatus for examining a sample according to the invention comprises: a spectroscopic analysis instrument including a component that places a surface portion of the sample in different electrical charge states, for performing a first spectroscopic analysis of a surface portion of the sample when the sample surface portion is in a first electrical charge state and performing a second spectroscopic analysis of the surface portion of the sample when the sample surface portion is in a second electrical charge state different from the first electrical charge state; and a comparator coupled to the instrument to compare the first spectroscopic analysis result with the second spectroscopic analysis result to obtain at least one of structural and electrical information about the sample, wherein the component is operative for giving the first and second electrical charge states values that enable information to be obtained about sample structural features having dimensions of less than 50 nm.

Another embodiment of apparatus for examining a sample according to the invention comprises: a spectroscopic analysis instrument including a component that places a surface portion of the sample in different electrical charge states, for performing a first spectroscopic analysis of a surface portion of the sample when the sample surface portion is in a first electrical charge state and performing a second spectroscopic analysis of the surface portion of the sample when the sample surface portion is in a second electrical charge state different from the first electrical charge state; and an arithmetic unit coupled to the instrument to compare the first spectroscopic analysis result with the second spectroscopic analysis result to obtain at least one of structural and electrical information about the sample, wherein each spectroscopic analysis result contains data identifying a characteristic of the spectral response for each of at least two elements contained in the sample, and the comparison performed by the arithmetic unit includes the steps of determining, for each of the at least two elements contained in the sample, a difference between the first spectroscopic analysis result and the second spectroscopic analysis result and correlating the differences determined in the determining step for the at least two elements to provide a quantitative value of a characteristic of the sample.

In one aspect, the invention provides a method for depth profiling of a sample consisting of a thin layer of dielectric material on a conducting substrate using controlled surface charging in electron spectroscopy. The term "depth profiling" as used herein refers to the determination of the chemical composition of a sample in the direction perpendicular to the sample surface.

For depth profiling, the sample to be examined should be not more than 20 nm thick and preferably not more than 10 nm thick. The dielectric material may be, for example, without being limited to, ceramic materials (e.g. alumina), silica, metal oxides, polymers, organic multilayers and biological molecules. The conducting substrate may be of a metal, e.g. Au and Ag, or a semiconductor, e.g. Si, GaAs, or $TiO_2$. The sample may be excited with any suitable irradiation source such as X-ray, electron beam, and UV, and the low energy source may be any suitable source such as electron beam or ion beam source. Procedures using an electron beam source will be described below. An ion beam source can be used in it the same way to produce different positive surface charge states. This will produce spectral peak shifts in the opposite direction from those produced by an electron beam source. The ion beam may be an $AR^+$ source. The use of such a source to neutralize surface charge is described in Nelson et al, "Surface charge neutralization of insulating samples in x-ray photoemission spectroscopy", J. Vac. Sci. Technol. A 16(6), Nov/Dec 1998, 3483–89.

According to one embodiment of the present invention, a novel application of XPS is presented, where accurate depth information is obtained from measured photoelectron energy values. Excess negative charge, stabilized on the surface of a dielectric overlayer by application of an electron flood gun, creates controllable potential gradients along the depth axis; the local potential is probed directly via XPS line shifts, providing the depth position of the atoms. This approach is described below with reference to self-assembled multilayers on gold surfaces, where marker monolayers are inserted at predetermined depths. Nanometer depth resolution, obtained on a linear energy scale, is shown, in excellent agreement with traditional line intensity analysis.

The examples presented hereinbelow use X-ray photoelectron spectroscopy (XPS). However, Auger electron spectroscopy (AES), scanning Auger, UPS, SEE and other spectroscopies may be appropriate. Local potential gradients are projected on the electron spectrum, thus providing unique structural and electrical information. The method is suitable for analyzing interfacial structures on the nanometer scale, including very thin films.

In another aspect, the invention makes use of known surface charging phenomena to analyze self-assembled (SA) monolayers on heterogeneous substrates, providing lateral resolution on a scale given by the substrate structural variations, i.e., much smaller than the probe size[10]. This aspect of the invention provides a simple approach where the superior depth resolution of XPS is used to gain lateral sensitivity to surface structural variations that meets the above requirements. It is based on controlled variation of a selected parameter, the excess surface charge, which is sensitive to differences in the local conductivity.

According to this aspect, XPS is used to analyze mesoscopic systems at a lateral resolution given by the substrate structure. The method is based on controlled differential charging of multi-component surfaces, using the electron flood gun or an analogous device.

With nm-size surface features, surface conductivity, adhesion quality, geometrical factors, etc., are complicating factors. Nevertheless, the resultant excess charge produced by the electron flood gun, and accordingly the XPS line shifts, provide a powerful tool for site classification in patterned surfaces. In contrast to the low level naturally occurring positive charging that occurs in mesoscopic structures, which is usually insufficient for satisfactory analysis, the use of the flood gun at relatively high fluxes, producing negative excess charge, leads to larger and well-controlled spectral line shifts, required for quantitative analysis and site classification.

Procedures according to this aspect of the invention can serve to obtain integral information, namely, differentiating between portions of the measured area. The emphasis here is on the correlation between a substrate and overlayers thereon. Hence, an important application would be the examination of a patterned substrate onto which a certain overlayer is applied. The method allows to separately analyze the overlayer on each of the different parts of the substrate.

As will become apparent from the following detailed description, methods according to the invention can serve a variety of purposes including, but not limited to, the following examples: determination of the breakdown voltages across thin dielectric layers; this is relevant to ultrathin capacitors, electronic devices, etc; quality control in integrated circuits; analysis of thin polymer films, with minimal induced damage; multilayer structures (design of new optoelectronic materials, biosensors, heterogeneous catalysts, etc.) including depth profiling and electrical tests; study of adsorption and layer formation on heterogeneous substrates; differentiation of species which are spectrally similar; analysis of lateral distribution of materials/elements on a surface (chip); and testing the electrical conduction and connectivity on microchips.

By proper selection of flood gun flux and bias voltage levels, the invention allows information, including qualitative information to be obtained for samples having lateral or depth features smaller than 50 nm, preferably smaller than 10 nm, and even smaller than 5 nm. Quantitative information can be obtained on the basis of relationships between two or more elements in the sample with respect to the binding energy level shifts in associated spectral response peaks resulting from changes in surface charge state.

BRIEF DESCRIPTION OF THE DRAWING

FIG. 2 is a series of curves illustrating spectral responses produced during analysis procedures according to the invention.

FIGS. 6a–d are curves showing XPS results, and specifically intensity in units of counts per second vs. binding energy in eV, for a DT+OTS monolayer on the composite Au—SiO$_2$ surface, showing narrow scans for Au, O, Si and S and line decomposition for O (FIG. 2b). In each Figure, the top and bottom curves correspond, respectively, to 'gun-off' and 'gun-on' conditions.

FIGS. 7a–b are curves showing XPS results, and specifically intensity in units of counts per second vs. binding energy in eV, for the DT+OTS monolayer on the composite Au—SiO$_2$ surface, showing narrow scans and line decomposition for C. FIG. 7a represents the 'gun-off' condition and FIG. 7b represents the 'gun-on' condition.

DETAILED DESCRIPTION OF THE INVENTION

Figure 1:
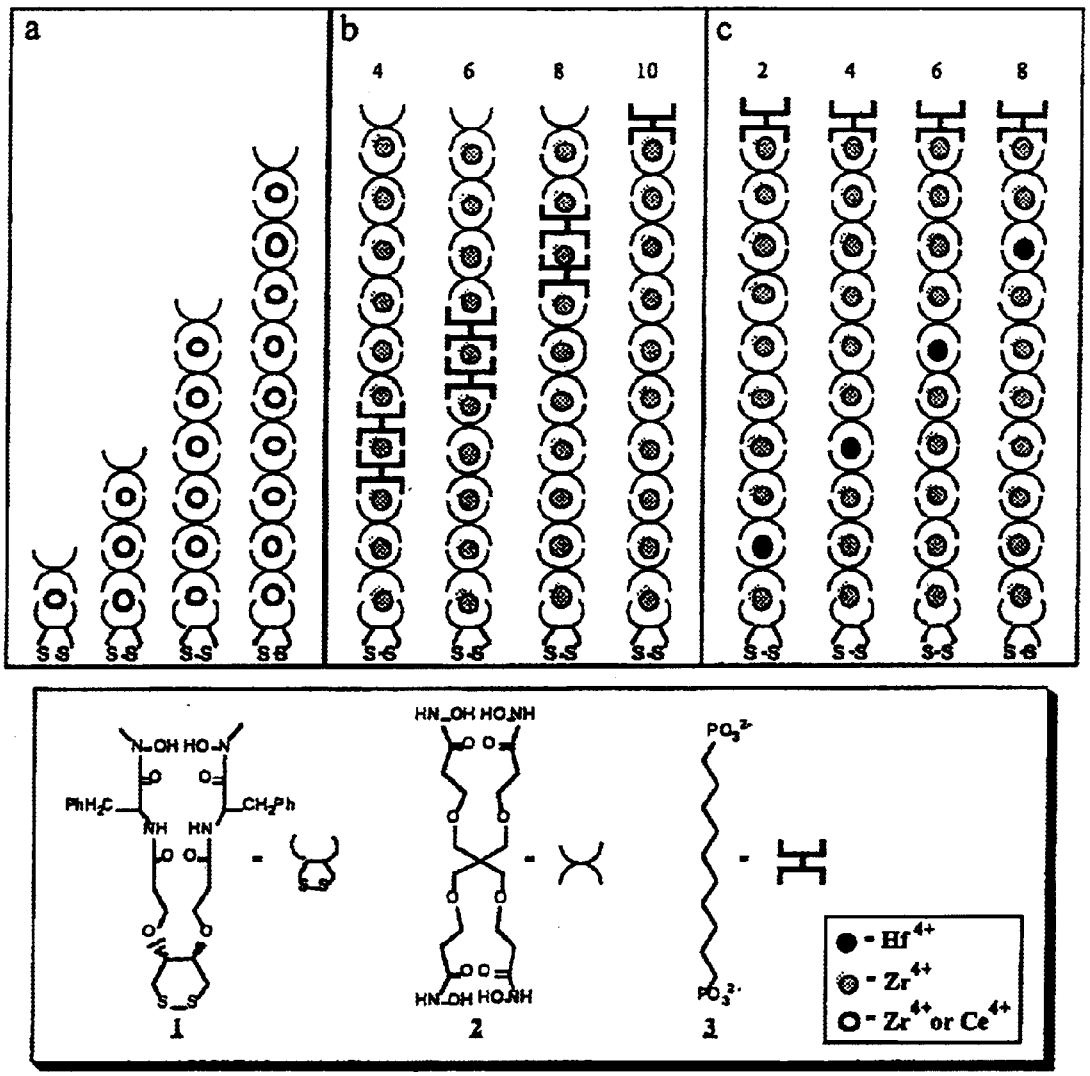
FIG. 1 is a schematic presentation of multilayer systems that can be the subject of depth profile studies according to the invention.

The present invention provides a simple, yet powerful, new application of XPS, where information provided by discharge processes is used to achieve nanometer-scale resolution in the depth direction of a sample, such as a substrate. The method is applicable to dielectric layers on conducting surfaces. In this new application we induce controlled surface charging (CSC) to the sample, e.g., by use of an electron flood gun. This results in the development of differential potentials in the studied systems, which are reflected in the measured kinetic energy of photoelectrons, thus providing the spatial position of the atoms. These unique data, combined with the chemical analysis capabilities of XPS, allow to elucidate the depth direction composition in the case of a laterally-uniform dielectric layer. The measured XPS line shifts are, therefore, directly translated to depth-profiling, with nanometer-scale resolution.

The method is also applicable to a large variety of systems, including mixed conducting-insulating surfaces, to provide lateral resolution as will be described below and as described in a publication[13] published on May 3, 2000, describing work done by the present inventors and the entirety of which is incorporated herein by reference.

The application of the CSC method for depth profiling and for lateral differentiation, when the two methods complement each other, form the basis for a comprehensive three-dimensional analysis of interfacial it structures.

The method of the invention has many applications including: (i) determination of the breakdown voltages across thin dielectric layers, that is relevant for ultrathin capacitors, electronic devices, etc; (ii) quality control in electronic circuits; (iii) analysis of thin polymer films with minimal induced damage; (iv) multilayer structures (design of new optoelectronic materials, biosensors, heterogeneous catalysts) including depth profiling and electrical tests; (v) study of adsorption and layer formation on heterogeneous substrates; (vi) differentiation of species which are spectrally similar.

The information that is obtained may be used, depending on the substrate, for depth profiling or for lateral differentiation.

Simple examples of the practice of the invention are as follows: if the substrate is a printed circuit which is supposed to have a continuous conducting strip on it, the present invention can provide information about whether or not by there is a break in the conducting strip. Thus, if the peak for the conducting metal shows no shift, then that means the entire conducting layer is grounded, and so there will be no charge difference between the two measurements. When there are differences in the conducting material peaks, then it is apparent that there is a portion of the conducting material that is not grounded and whose potential changes between the two measurements. Thus the substrate can be discarded as having a defect.

Another example is the determination of whether one material is in contact with another material on the surface of the substrate. Thus, for example, sulfur deposited on a gold portion of the substrate will not show a difference between the two spectra, but sulfur applied to a dielectric portion of the substrate will show a change, a shift.

For depth profiling, if there is, for example, a conductive bottom layer having a dielectric material deposited thereon, one can determine the depth of different elements within this dielectric material by the magnitude of the shifts. Thus, the deeper it is, the smaller the magnitude of the shift. Thus, one can get a vertical distribution map of the different elements of the dielectric.

It is not absolutely necessary that the conducting layer be the bottom layer.

A system for carrying out the methods of the invention includes a conventional electron spectroscopy equipment, e.g. XPS, with certain modifications, including: (1) a computer-controlled electron flood gun (kinetic energy with broad energy range; flux), enabling well-defined FE conditions and (slow) modulation capabilities with reliable phase control; (2) sample current detection (nano-amp sensitivity); (3) fast and flexible sample handling and transformation to/from the vacuum chamber (automated); (4) parallel spectrum detection (desirable); (5) software—correlation calculations, optimization, curve fitting, specific software for line intensity calculations; (6) positive charging (low energy ion flux); (7) small area measurements (for, e.g., integrated circuit analysis). Devices of the type described above and software capable of performing the described procedures are already known in the art.

The application of the CSC method for depth profiling and to obtain nanometer-scale depth resolution in laterally homogeneous structures will be described below.

Well-defined correlation between the local potential and the depth axis can be achieved, e.g., in systems comprising an insulating overlayer on a grounded metallic substrate, where the overlayer is laterally uniform. In the practice of the present invention, the flood electron gun is not used for charge neutralization, but is operated at a considerably higher electron flux than that used for charge neutralization, creating a dynamic balance between charge generation and discharge rates, which is controlled by variation of the flood gun parameters, i.e., electron flux and kinetic energy. Extra negative charge is accumulated on the film surface, and a dynamic steady state is reached where the charge leakage to the grounded substrate is balanced by the net incoming flux. With the systems described herein, essentially no space charge is developed within the dielectric film. The resultant depth field is therefore constant, such that the local potential, correlated directly with XPS line shifts, varies linearly with the depth scale (z). The steady-state situation, with a surface charge density C and an overlayer dielectric constant ∈, is thus modeled by a parallel-plate capacitor, where the local potential ϕ between the plates is given by equation [1] (σ is determined by the overlayer resistivity and the flood-gun operating conditions).

$$\phi(z) = 4\pi\sigma z/\in \quad [1]$$

The studied substrates comprised a 100 nm {111} textured gold layer, evaporated on a highly-polished doped Si (111) wafer[14]. Metal-organic coordinated multilayers were constructed layer-by-layer on the gold surface as described in reference 14 and as will be described below.

FIG. 1 includes sections a, b and c that schematically depict the various multilayer structures that were studied. Each vertical column in each of sections a–c represents a full multilayer. The bold symbols represent marker units. The numbers at the tops of the columns sections b and c indicate the position of the marker units in those columns, corresponding to the abscissa of FIG. 4. The bottom section of FIG. 1 shows structural formulas for the various molecules making up the multilayer structures. The first layer of each multilayer group is a disulfide-bishydroxamate molecule, $1^{15}$ whose disulfide group binds the associated multilayer structure to the Au substrate. The other layers are constructed of two different bifunctional ligand repeat units: a tetrahydroxamate 2;[14] and a diphosphonate 3, [16-18]. Every pair of layers was connected by a selected one of three different tetravalent metal ions: $Zr^{4+}$, $Ce^{4+}$ or $Hf^{4+}$, represented by the symbols in the lower section of FIG. 1. XPS measurements were carried out on substrates carrying each of the twelve multilayer structures shown in sections a, b and c, with a Kratos Analytical AXIS-HS Instrument, which is a standard instrument found in almost every surface analysis lab, using a monochromatized Al (Kα) source (hv=1486.6 eV) at a relatively low power[13], i.e., a source intensity of 5 mA, 15 kV, the instrument being equipped with a flood gun. In the performance of the examinations described below, the beam directed at the substrate had a diameter of ca. 3×3 mm and impinged on a fixed area of the sample, i.e., the beam did not scan the sample surface. The size and location of the analyzed area was determined by the photoelectron collection optics and here was ca. 0.8 mm in diameter. Newer systems that are available can analyze sample areas down to ca. 1 μm in diameter. The collection time for each observation is highly dependent on the signals analyzed.

The instrument described above, as well as other spectroscopic instruments on the market, includes an electron flood gun as a standard component.

Various measurements were carried out using different ones of the following flood gun emission current and bias voltage conditions: (0) gun off; (1) 1.90 mA, −1.5 V (2) 1.90 mA, −2.7 V; (3) 1.90 mA, −3.2 V.

FIG. 2 show spectral response curves for these measurements in terms of intensity vs. binding energy in eV. The ordinate is in units of counts/second in each energy channel.

For a general demonstration of CSC, two sets of multilayers with varying thicknesses (2 to 10 layers) were constructed (FIG. 1a), using the tetrahydroxamate ligand 2. Each set was assembled with a different binding ion, i.e., Zr(IV) or Ce(IV), respectively.

FIG. 2a shows the spectral response of a 10-layer multilayer on gold with Zr(IV) ions, the right-hand structure in section a of FIG. 1 under flood gun conditions 0 and 2. The various surface elements manifest energy shifts and line-shape changes, both associated with the development of potential gradients perpendicular to the sample surface: The Au(4f) line shifts by a very small amount, attributed to the finite sample dependent conductivity of the silicon substrate. All other overlayer elements exhibit much larger shifts, with differences correlated with their spatial (depth) distribution. The energy shifts and line shapes of elements not shown in FIG. 2 (N, O) are fully consistent with the model. Line-shape changes of the Zr(3d) doublet are shown, where the curve obtained under gun condition 0 is shown in dotted lines and is shifted by −1.96 eV. In other words, the dotted line curve, as shown in FIG. 2a, has been shifted from the position represented by the raw data. Curve fitting of the curve obtained under gun condition 2 is shown, using three free parameters for the single Gaussian and only two parameters, interlayer shift and attenuation to correlate the nine doublets, corresponding to the discrete ion layers. The curves shown to a smaller scale in FIG. 2a represent raw data for representative elements Au, O,Zr and C under flood gun conditions 0 and 2.

FIG. 2b shows the spectral response of an 11-layer Zr(IV)-based multilayer with two markers, Hf(IV) and the diphosphonate 3, multilayer 4 in section c of FIG. 1, where the Hf(IV) marker is in the fourth layer, which is the layer marked "4" in section c of FIG. 1. Raw data of representative elements are shown in the different portions of FIG. 2b at flood gun conditions 0, 1 and 3. In addition, the two lower portions of FIG. 2b, which show the spectral responses of Hf and P, also include curves 3* obtained under flood gun condition 3 for a similar multilayer with the Hf(IV) in the sixth layer which is the layer marked "6" in section c of FIG. 1.

Accurate determination of line shifts was achieved by graphically shifting lines until a statistically optimal match was obtained. This procedure, correlating the full line shape (100–200 data points), allowed excellent accuracy (~0.03 eV) in the determination of energy shifts, much beyond the experimental energy resolution (i.e., source and bare line widths). In cases where the external charging induced line shape changes, larger uncertainties were considered. The shifts were translated to potential differences relative to the gold by subtracting the corresponding gold line shifts. Special effort was made to determine time periods characteristic of the stabilization of local potentials, generally longer for the lower flood gun flux value, which in the example being described here is the value associated with flood gun condition 1. This was of particular importance in view of beam-induced damage[5], observed after an hour or more and found to slightly distort the CSC behavior.

In the two sets of samples described above, all the overlayer elements (except sulfur) are distributed along the depth scale, complicating the derivation of local potentials, and specifically the overall potential difference, $V_0$, developed across the entire overlayer and here relative to the 'gun-off' situation. Yet, an approximate analysis can be carried out by curve-fitting the metal ion lines to sets of discrete signals, corresponding to ion interlayer at progressive depth positions. The Zr(3d) doublet in FIG. 2a indeed exhibits asymmetric broadening under the 'gun-on' conditions, in contrast with the 'gun-off' situation where potential gradients, of opposite sign, are much smaller, thus having minimal effect on the line shape. The curve fitting of the 'gun-on' line for the Zr(3d) doublet in FIG. 2a yields energy shifts of 0.18 eV/layer and an intensity attenuation factor of 1.72/layer, in good agreement with further results given below. Hence, even without elaborate curve fitting, the Zr (and similarly, the Ce) line can provide an approximate value of $V_0$ from the shift of the low binding energy side of the line, rather than the peak, corresponding to the uppermost layer with the largest shift. The potential gradient in the 'gun-off' situation is much smaller, ~0.035 eV/layer, determined from curve fitting of the 'gun-off' lines (not shown). Consideration of these small gradients would increase the derived $V_0$ values by $\leq 10\%$.

Figure 3:
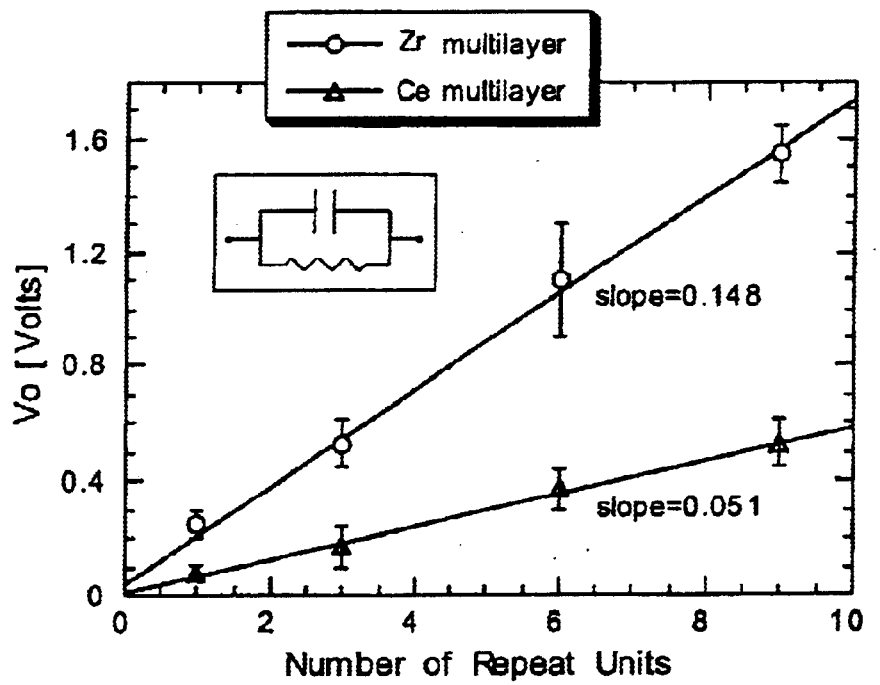
FIG. 3 is a graph illustrating the determination of layer thickness according to the invention.

FIG. 3 is a plot of $V_0$, the total potential difference across the multilayer structure vs. multilayer thickness, in terms of the number of molecular layers in the multilayer structure $V_0$ is derived from the Zr(3d) low binding energy side. The inset of FIG. 3 shows an electrical equivalent circuit of the multilayer structure, which is a simple parallel-plate capacitor and a shunt resistor.

The results presented in FIG. 3 allow two conclusions to be drawn. First, the potential difference across the full multilayer structure, $V_0$, increases linearly with multilayer structure thickness, suggesting that the multilayer structure itself is practically free of space charge. The system may, therefore, be satisfactorily simulated by the simple electrical circuit in the FIG. 3 inset. Second, the absolute gradient values, associated with the film resistivity in the depth direction, are medium sensitive; the nearly threefold difference in the slope of $V_0$ vs. film thickness between Zr(IV) and Ce(IV) suggests a marked influence of the binding ion on the electrical conductivity of it the layer. This emphasizes the power of the CSC method in analyzing electrical properties of ultrathin films.

Enhanced accuracy of CSC depth profiling is demonstrated with two additional sets of tetrahydroxamate-based coordination multilayers, where the energy shift of an indicator atom, installed at a well defined depth, is normalized to $V_0$, eliminating the effect of conductivity on the geometric information. Both sets comprised 11-layer films (including the base layer), with Zr(IV) as the binding ion. A full quantitative treatment is achieved with the first set when two markers are used, as shown in section c of FIG. 1; the value of $V_0$ is accurately determined with a diphosphonate layer positioned at the film top, while Hf(IV) serves as the 'moving' marker, replacing a Zr(IV) layer at a different depth in each sample. The Au substrate is always a third marker. The second set was designed to confirm the structural and electrical compatibility of diphosphonate linkers with the tetrahydroxamate multilayer; here diphosphonates, inserted at progressive depths, as shown in section b of FIG. 1, serve as the marker layer, while $V_0$ is derived, as discussed above with reference to FIG. 2, from the shift of the low binding energy side of the Zr(IV) lines. Diphosphonate bilayers, rather than monolayers, were used, except for the top layer position, as shown in section b of FIG. 1, in order to increase the P signal intensity.

Figure 4:
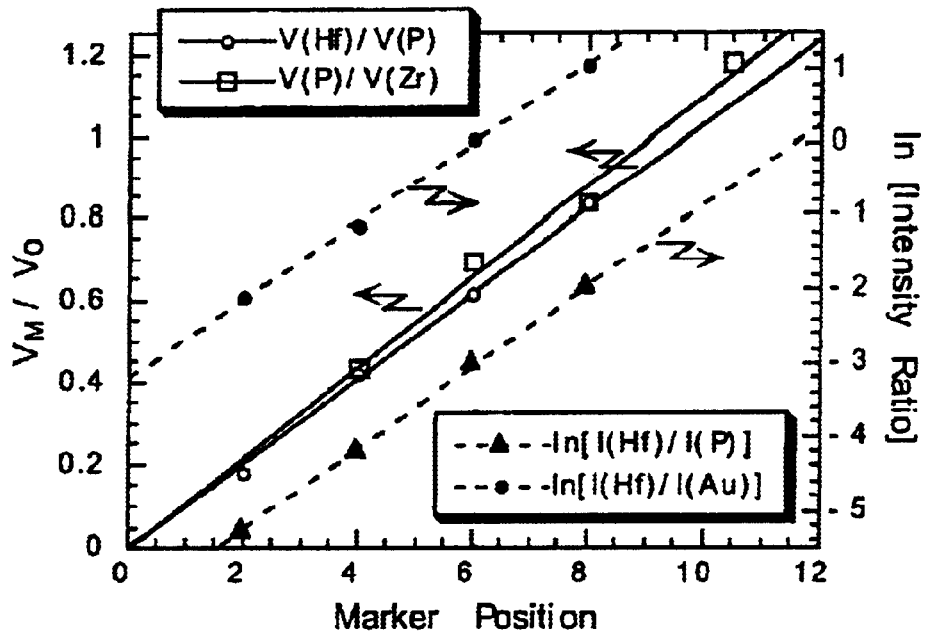
FIG. 4 is a graph illustrating the results of depth profiling according to the invention with accurately positioned markers.

FIG. 4 is a graph showing, in solid lines, the normalized local potentials, $V_M/V_0$, of multilayer structures for different marker positions vs. marker position, for P and Hf markers in the multilayers shown in sections b and c of FIG. 1, respectively, on a linear scale, and, in dashed lines, the depth analysis via line intensities for the multilayers shown in section c of FIG. 1, on a log scale. The films with Hf(IV) in position 2, the left-hand column in section c of FIG. 1, displayed weak Hf signals that required second derivative data processing for reliable determination of the energy shifts. While FIG. 2b shows selected spectra, the complete results are summarized in FIG. 4 and show linear behavior of the normalized shifts, yielding values within 5% of the expected geometric positions (10% for the samples with Hf(IV) in position 2). Hence, the energy shifts can be directly converted to depth information on a linear scale and with an accuracy on the order of a single layer thickness, in the present case ca. 1 nm. The results again justify the use of the simple capacitor model suggested above for the local potential in these systems. Moreover, the agreement between the two sets shows the reliability of the CSC method.

To compare these results with the traditional intensity-based depth profiling, the P, Hf and Au line intensities were quantified. As shown in FIG. 4, good exponential dependence is obtained for the intensity ratios, indicating the high regularity of the studied structures, as previously reported[14]. The excellent agreement between the two independent depth profiling approaches serves to substantiate the CSC results. Note the in-situ derivation of the attenuation factor obtained from FIG. 4, $d/\lambda=0.54$, where d is the single layer thickness and $\lambda$ the relevant inelastic mean free path (at kinetic energies of 1300–1400 eV), calculated here to be 2.73 nm. This value of λ is relatively small compared with values reported for organic media[6], a result believed to originate from the presence of the metal ions.

In summary, the first aspect of the invention, as described above, provides a simple and convenient method for non-destructive XPS depth profiling based on controlled surface charging induced by the electron flood gun. The dielectric overlayers under study exhibit a dynamic steady-state situation, where charge is accumulated at the film-ambient interface and is discharged to the substrate, creating a controllable potential drop across the film. XPS line shifts, induced by modulating the charging conditions, correlate with the atomic positions in the depth direction, thus providing quantitative depth profiling with nanometer depth resolution. The multilayers studied here are unique in allowing installation of several markers at well-defined positions. The combination of an analytical probe and a molecular system, exhibiting optimally matched length scales, demonstrate the capabilities of the new approach.

As a high-resolution depth profiling method, CSC is applicable to a large variety of non-conducting layers in the <~10 nm thickness range. Moreover, the present results suggest interesting applications of CSC as a contactless electrical probe, capable of direct detection of local potentials in thin overlayers. In light of recent progress in enhancing XPS lateral resolution, which relates to the second aspect of the invention, CSC may be an effective tool for studying 3-D nanostructures and molecular architectures.

Lateral differentiation according to the invention is demonstrated here with a mixed organic monolayer (thiol and silane molecules) self-assembled on a novel composite surface, the latter comprising a conductive substrate (Au) with a non-uniform insulating overlayer ($SiO_2$ islands). Upon varying the flood-gun electron flux, the dynamic balance of accumulated local surface charge is modified, exhibiting line shifts which can be correlated with the surface structure. As described below, a qualitative interpretation of line shifts can provide quantitative information on the surface composition and morphology, e.g., unequivocally correlating adsorbed molecules with specific surface sites.

Composite Au—$SiO_2$ surfaces were prepared by controlled diffusion of Si through a gold layer.[30, 31] When a gold film (50–100 nm thick) is evaporated onto an oxide-free (H-passivated) surface of a Si wafer and then heated (to ca. 100–150° C.) in an oxygen-containing atmosphere, formation of a $SiO_2$ overlayer on top of the Au film is observed. The process involves diffusion of Si atoms through the Au film to reach the Au/ambient interface, where the Si atoms are oxidized to form $SiO_2$ islands. If the process is continued, a $SiO_2$ film would form. When Au is evaporated on oxide-covered Si, the tendency of Si atoms to diffuse through the Au film is effectively suppressed. Careful adjustment of the parameters (temperature and duration of heating, Au film thickness, oxygen and moisture content in the contacting gas, Si crystallographic face) provides controlled size and distribution of the insulating islands.

More specifically, the samples were prepared by resistive evaporation of 50 nm {111}-textured Au onto HF-etched (H-passivated) highly-polished Si (111) surfaces, followed by annealing in air for 24 min at 150° C., followed by cooling in air to room temperature. The two surface components (Au and $SiO_2$) differ in both chemical reactivity and electrical conductivity, allowing subsequent assembly of different molecules at different surface sites, and to the creation of differential charging.

The surface of a sample prepared as described above was pretreated with UV-ozone+ethanol dip[32]. Then, decanethiol (DT) was adsorbed for 2 h, in a 4 mM solution in bicyclohexyl, and the sample rinsed with chloroform, followed by octadecane trichlorosilane (OTS) adsorption for 2 min in a 2 mM solution in bicyclohexyl, and then rinsing with chloroform. The DT molecules bind selectively to Au and the OTS molecules bind selectively to the $SiO_2$.

Figure 5:
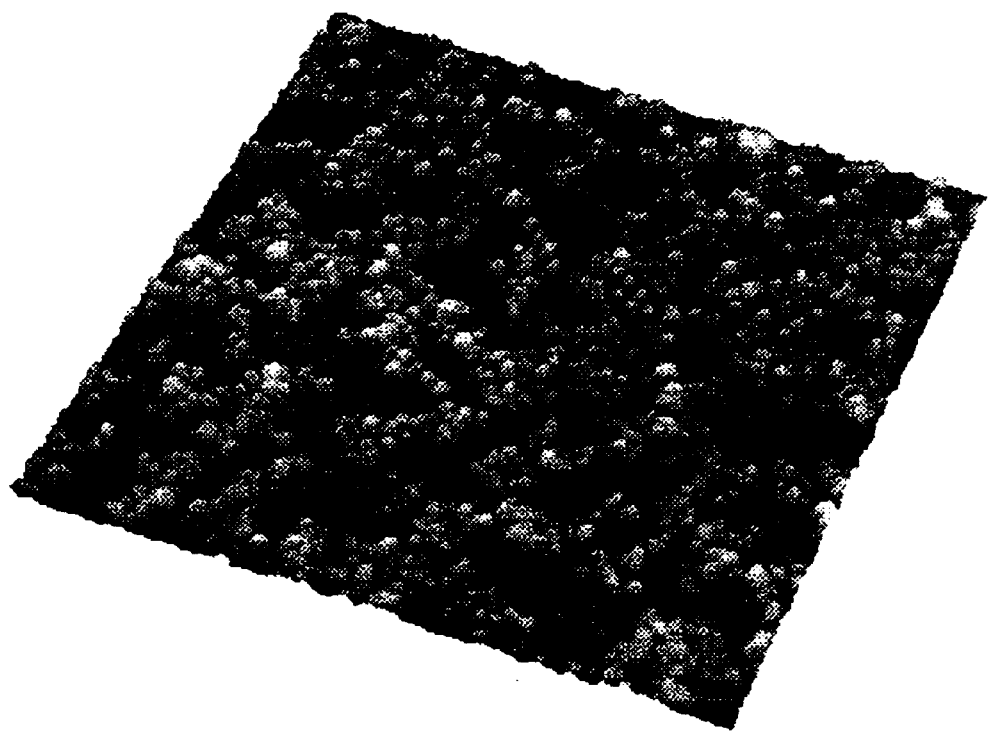
FIG. 5 is an intermittent contact mode SFM image (5 μm scan; z-range, 54 nm) of a composite Au—SiO$_2$ surface after self-assembly of DT+OTS.

FIG. 5 shows a scanning force microscope (SFM) image of the composite Au—$SiO_2$ surface after self-assembly of the mixed monolayer (DT+OTS). The $SiO_2$ phase appears as grains, of 20–30 nm average height and 50–70 nm average diameter, aggregated into larger clusters, randomly distributed on the Au surface. The average diameter of the grains was measured over individual grains after erosion of it the microscope tip, obtained from the image by blind reconstruction (software developed by A. Efimov, available as freeware at www.siliconmdt.com). This procedure gives an upper bound for the true feature size, and yields diameters 20–40 nm smaller than those measured on the raw image.

XPS data were collected with the AXIS-HS Kratos instrument described earlier herein, using a monochromatized Al($k_\alpha$) source, all operating conditions being as described earlier herein. To eliminate beam-induced damage,[5] a low source intensity (5 mA, 15 kV) and relatively short scans were used.

The spectra in FIGS. 6 and 7 represent a compromise in signal-to-noise ratio (SNR) required for damage-free data collection. Scanning conditions were determined after systematic study of the damage evolution and its characteristic time scales. Data analysis and conclusions were based on comparison with longer measurements, i.e., improved SNR (not shown), performed after the short scans.

The flood-gun flux was controlled with respect to its emission current and two bias voltages. Two extreme cases are considered: 'gun-on' (emission current, 1.90 mA; bias, 1.0 and 2.7 V), and 'gun-off' (zero electron flux). In the former case, a relatively large negative excess charge is supplied to the surface, a typical integrated sample current being ca. −300 nA. In the latter case, a small positive charge is created, resulting from the photoemission events, a typical sample current being ca. 1–4 nA). Intermediate flood-gun operating conditions were also tested, showing consistent results (not shown). Data analysis included Shirley background subtraction and Gaussian-Lorenzian line shapes for curve fitting, which are known in the art.

The spectral response to the flood-gun flux is demonstrated in FIGS. 6 and 7. The Au (4f) line exhibits no spectral shift, reflecting the good charge compensation across the metallic layer and the silicon wafer on which the gold film was evaporated. In contrast, the Si (2s) and O (1s) lines shift by ca. 2 eV, attributed to the poor conductivity of the silica grains. This effect forms the basis for the site resolution of the spectrally similar adsorbed molecules. Indeed, the C (1s) line splits into several components, subjected to different shifts, as shown in FIGS. 7a and 7b, which resemble those of the corresponding substrate signals: $C_{DT}$, exhibiting a negligible shift, is attributed to the molecules adsorbed on gold; $C_{OTS}^1$ and $C_{OTS}^2$ are highly shifted components, attributed to the molecules located on different silica sites, as will be discussed below. Note that, as shown in FIG. 6c, the S (2p) line does not shift, confirming its close proximity to the gold substrate, consistent with the it adsorption selectivity of the gold for DT molecules. The extracted overall shifts, i.e., 'gun-off' vs. 'gun-on' peak positions, are given in Table 1, below:

Table 1. Atomic concentrations and energy shifts from XPS results for the DT+OTS monolayer on the composite Au—SiO$_2$ surface. The peak shifts correspond to 'gun-on' vs. 'gun-off' measurements (FIGS. 6 and 7).

|  | Au | S | Si | O | C |
|---|---|---|---|---|---|
| Total conc. % | 29.4 | 1.4 | 8.45 | 16.1 | 44.65 |
| Peak shift (eV) | 0.0 | ≦0.05 | 1.8 | 1.8 | 0.7 |

|  | O$^1$ | O$^2$ | C$_{DT}$ | C$_{OTS}^1$ | C$_{OTS}^2$ | C$_{Im}$ |
|---|---|---|---|---|---|---|
| Line decomposition relative conc. % | 48.5 | 51.5 | 36.8 | 28.9 | 30.3 | 4.1 |
| Line decomposition peak shift (eV) | 1.25 | 2.2 | 0.2 | 1.2 | 2.25 | 2.6 |

In addition, several blank experiments were carried out with blank samples (i.e., before monolayer self-assembly). The spectral shifts obtained with these blank samples are in good agreement with the results in Table 1. Electrical isolation of the sample holder almost completely removes the differential effects.

The 'gun-off' spectral lines are relatively narrow, indicating minor surface potential variations. Yet, accumulation of some excess positive charge on the silica surface is manifested as an asymmetric broadening of the carbon line toward the high binding energy side. The curve fittings for the 'gun-off' measurements are, therefore, less determining than the 'gun-on' ones. In the 'gun-on' spectra, the silica signals reflect grain inhomogeneity. At least two distinct components within the O line (O$^1$ and O$^2$, FIG. 6b) suggest the existence of two major types of silica grains, subjected to different discharge routes. The existence of 'second layer' grains has been suggested by AFM measurements. The relative abundance of the two components depends on the sample preparation details, and will not be discussed here. Inclusion of a third component is not justified by the curve fitting; decomposition of the Si line (not shown) is in full agreement with the two-component analysis. This argument is MS further supported by the C (1s) line decomposition, where the two major shifted components, C$_{OTS}^1$ and C$_{OTS}^2$, are well correlated with the silica energy shifts, O$^1$ and O$^2$ (Table 1).

The results discussed above clearly reveal the site selectivity. However, the power of the CSC method is greatly enhanced by full quantitative analysis of line intensities, where simultaneous agreement of line shifts and intensities would provide a firm confirmation of the qualitative analysis. It should be realized, though, that such an analysis is model-dependent.

The first-order model used here assumes rectangular silica grains on a thick gold layer, with average grain height (D) much larger than the relevant electron mean free path ($\lambda$). The fraction of gold surface covered with silica is denoted $\theta$. DT molecules are assumed to bind selectively to the gold at a relative coverage $\theta_{DT}$, with a layer thickness 1.8 times smaller than that of the OTS fraction, the latter being selectively bound to the silica at a relative coverage $\theta_{OTS}$. Extraction of the coverage parameters was carried out by fitting the theoretical expressions to the experimental element concentrations before line decomposition. The values obtained are: $\theta=0.53$; $\theta_{DT}=1.00$; $\theta_{OTS}=0.95$, with estimated relative errors, <5%, consistent with the expected site selectivity and suggesting nearly full coverage by the thiol and the silane. These results fully agree with the independently derived values of CDT: C$_{OTS}$ and C$_{DT}$:S, the latter verified by much longer scans, obtained from line decomposition. For accurate determination of the theoretical ratio C$_{DT}$:S, use was made of a discrete summation over the thiol C atoms, yielding $$\sum_{n=0}^{9} e^{-n\delta/\lambda} = (1-e^{-9\delta/\lambda})/(1-e^{-\delta/\lambda}),$$

where $\delta$ is the projection of the interatomic (C—C) distance along the vertical axis. The value of $\theta$ is in good agreement with independent measurements of the silica coverage.

The calculation was repeated with different model structures for the grains, e.g., grains with inclined side-faces. The calculated parameters converge within ±7%, exhibiting limited sensitivity to the chosen model structure. The 4% C$_{Im}$ signal appearing at 284.3 eV in the 'gun-on' curves of FIG. 7b, which is small within the present accuracy limitations, appears to originate from silica sites, and is attributed to a small amount of oxidized carbon contamination on the strongly shifted silica component. The weak signal observed around 286.9 eV in the 'gun-off' spectrum of FIG. 7a could arise from the same contamination. The possibility that C$_{Im}$ is related to grain edges, namely, to silica regions relatively close to the gold, is ruled out due to lack of a corresponding feature in the O line shape.

The estimated overall accuracy of the analysis is than ±10%. Note that accuracy is expected to improve substantially when applied to ordered, or patterned, substrates, where the complexity of solving the substrate and overlayer parameters simultaneously can be eliminated.

The lateral differentiation method according to the invention can be used to provide information about whether or not there is a break in a conducting strip on a printed circuit or IC when the strip is supposed to be continuous and grounded. If the spectral response peak for the conducting metal shows no shift between gun-on and gun-off spectral analyses, then that means the entire conducting strip is grounded, and so there will be no charge difference between the two measurements. When there is a difference between the conducting material spectral response peaks, then it is apparent that there is a portion of the conducting material that is not grounded and whose charge changes between the two measurements. Thus the substrate can be discarded as having a defect.

Another example is the determination of whether one material is in contact with another material on the surface of the substrate. Thus, for example, sulfur deposited on a gold portion of the substrate will not show a difference between the two spectra, but sulfur applied to a dielectric portion of the substrate will show a change, a shift.

Figure 8:
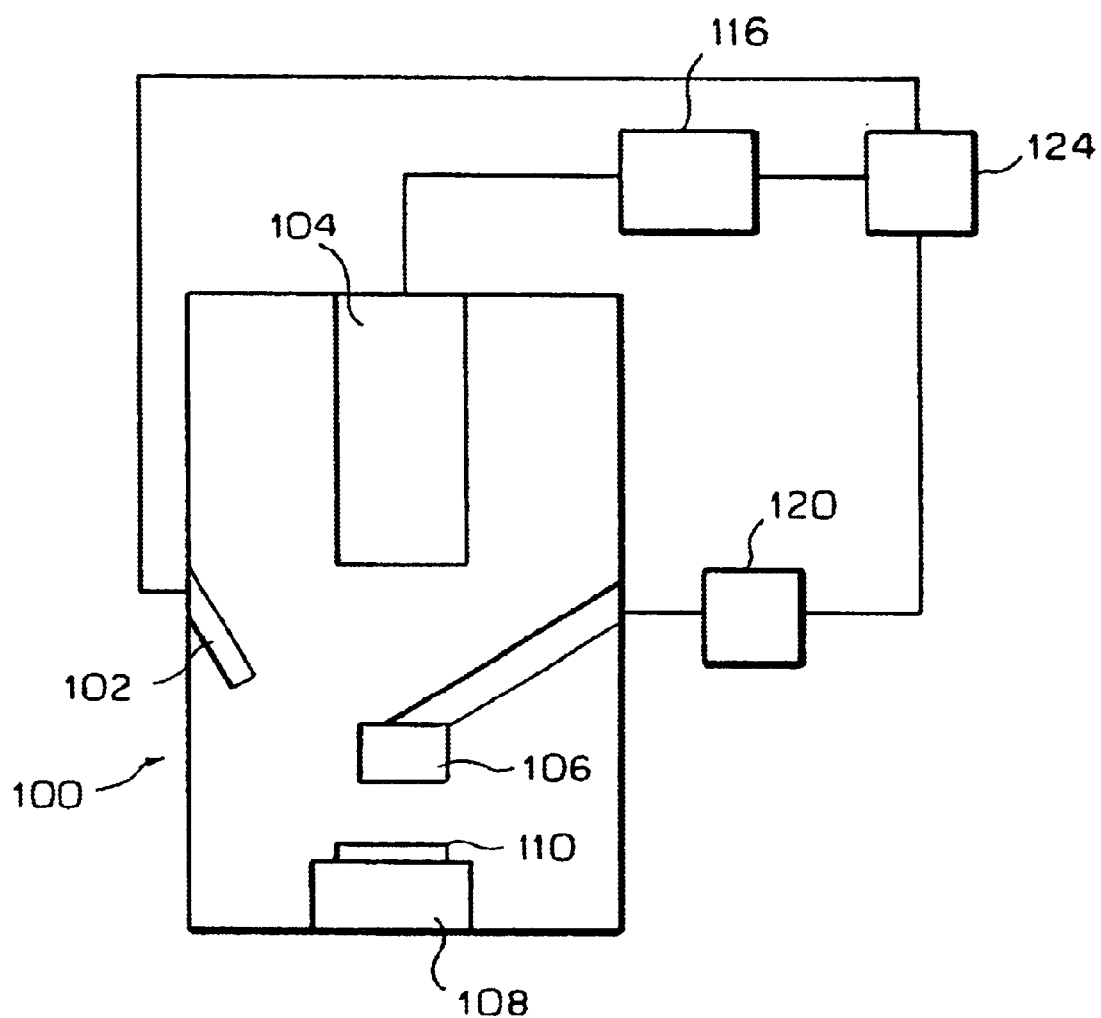
FIG. 8 is a pictorial view of one embodiment of apparatus according to the invention.

Thus, the lateral differentiation method according to the invention provides a powerful application of XPS, based on the information provided by discharge processes. The method is simple and exceedingly useful for analyzing complex systems, such as patterned surfaces presenting large variations in the local electrical conductivity. Controlled manipulation of a common XPS accessory—the flood gun—allows accurate site classification, translated to nanometer-scale lateral differentiation of multi-component overlayers. This approach is shown to provide quantitative analysis of disordered micro- or meso-scale features on composite macroscopic areas. In practice, the method was applied to a novel Au—SiO$_2$ surface, demonstrating molecular differentiation in a mixed monolayer on a composite surface. Application to well-defined (lithographic) heterostructures would simplify the analysis and improve its accuracy considerably, such that a true lateral resolution may be achieved. FIG. 8 is a simplified pictorial view of an embodiment of a system that can be employed to examine samples according to the present invention. This system includes a known XPS instrument 100, such as the Kratos instrument described earlier herein, equipped with an x-ray beam source 102, an analyzing and detection assembly 104, an electron flood gun 106 and a sample holder 108 on which a sample 110 to be examined is mounted. As is known, an x-ray beam produced by source 102 impinges on a region of the surface of sample 110, resulting in the emission of photoelectrons. With the aid of suitable electron optics provided in instrument 100, photoelectrons emerging from a selected portion of the sample region are directed into assembly 104, where they are analyzed. The resulting spectrographic information can be supplied to an electronic unit 116, where the resulting spectral analysis information can be stored. The operation of electron flood gun 106 can be controlled by a setting system 120 to vary the flood gun flux and bias voltage values in a desired manner. The x-ray beam produced by source 102 and the control signals produced by system 120 can be controlled by a master control unit 124, which can also be connected for bidirectional signal transfer with electronic unit 116. After spectral response data has been obtained for one flux gun state, unit 116 can supply a signal to control unit 124, which then supplies signals to system 120 to create a different flood gun state. Then, the desired spectral analysis data can be obtained at the new flood gun state and stored in unit 116. Unit 116 can also be equipped to effect the desired energy shift determinations with respect to each element that is relevant to the information the is to be obtained about the sample. Control unit 124 can also operate to control the power or intensity of the x-ray beam.

Thus, as indicated above, the flood gun parameters can be computer controlled. Software can be provided in, or associated with, electronic unit 116 to control processing of the spectral response data, including determining spectral peak shifts, or differences, from one flood gun state to another for each element of interest and computing quantitative sample characteristic values based on these differences for several elements. Examples of such determinations and computations have been provided herein with respect to depth observations (FIGS. 1–4) and lateral differentiation (FIGS. 5–7).

As noted earlier herein, positive charging can also be used for creating different electrical charge states. The apparatus of FIG. 8 could be supplied with an ion flood gun in place of, or in addition to, the electron flood gun. Sample examinations could then be performed with the creation of positive or negative electrical charge states in any sequence.

According to another possible implementation of the invention, a contact could be provided within the spectrometer chamber and could be remote controlled from outside so as to ground different parts of the substrate with very fine manipulation. In addition, in place of a flood gun, or guns, different areas of conductive material on the surface of the sample can each be connected to a respective contact and different voltages can be applied to each contact to create different electrical charge states in different parts of the sample surface.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . ." and "means for . . .", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

Endnotes
1. *Practical Surface Analysis* Vol. 1, $2^{nd}$ Edn., Briggs, D. & Seah, M. P. (Eds.), Wiley, New York, 1990.
2. Hofmann, S. Depth profiling in AES and XPS, in *Practical Surface Analysis* Vol. 1, $2^{nd}$ Edn., Briggs, D. and Seah, M. P. (Eds.), Wiley, New York, 1990,pp. 143–199.
3. Tougaard, S. Quantitative analysis of the inelastic background in surface electron spectroscopy. *Surf. Interf. Anal.* 11, 453–472 (1988).
4. Tyler, B. J., Castner, D. G. & Ratner, B. D. Regularization—A stable and accurate method for generating depth profiles from angle-dependent XPS data. *Surf. Interf. Anal.* 14, 443–450 (1989).
5. Frydman, E., Cohen, H., Maoz, R. & Sagiv, J. Monolayer damage in XPS measurements as evaluated by independent methods. *Langmuir* 13, 5089–5106 (1997).
6. Seah, M. P. Charge referencing techniques for insulators, in *Practical Surface Analysis* Vol. 1, $2^{nd}$ Edn., Briggs, D. & Seah, M. P. (Eds.), Wiley, New York, 1990,App. 2, pp. 541–554 and references therein.
7. Tielsch, B. J., Fulghum, J. E. & Surman, D. J. Differential charging in XPS. 2.Sample mounting and x-ray flux effects on heterogeneous samples. *Surf. Interf. Anal.* 24, 459–468 (1996).
8. Barr, T. L. Studies in differential charging. *J. Vac. Sci. Technol.* A 7, 1677–1683 (1989).
9. Lewis, R. T. & Kelley, M. A. Binding energy reference in XPS of Insulators. *J. Electron Spectrosc. Relat. Phenom.* 20, 105–115 (1980).
10. Miller, J. D., Harris, W. C. & Zajac, G. W. Composite interface analysis using voltage contrast XPS. *Surf. Interf. Anal.* 20, 977–983 (1993).
11. Beamson, G., Clark, D., Deegan, D. E., Hayes, N. W., Law, D. S-L., Rasmusson, J. R. & Salaneck, W. R. Characterization of PTFE on silicon wafer tribological transfer films by XPS, imaging XPS and AFM. *Surf. Interf. Anal.* 24, 204–210 (1996).
12. Barr, T. L. Applications of electron spectroscopy to heterogeneous catalysis, in *Practical Surface Analysis* Vol. 1, $2^{nd}$ Edn., Briggs, D. & Seah, M. P. (Eds.), Wiley, New York, 1990,p. 370.
13. Shabtai, K., Rubinstein, I., Cohen, S. & Cohen, H. High-resolution lateral differentiation using a macroscopic probe: XPS of organic monolayers on composite Au—$SiO_2$ surfaces. *J. Am. Chem. Soc* 122, 4959–4962 (2000).
14. Hatzor, A., Moav, T., Cohen, H., Matlis, S., Libman, J., Vaskevich, A., Shanzer, A. & Rubinstein, I. Coordination-controlled self-assembled multilayers on gold. *J. Am. Chem. Soc.* 120, 13469–13477 (1998).

15. Moav, T., Hatzor, A., Cohen, H., Libman, J., Rubinstein, I. & Shanzer, A. Coordination-based symmetric and asymmetric bilayers on gold surfaces. *Chem. Eur. J.* 4, 502–507 (1998).
16. Yang, H. C., Aoki, K., Hong, H.-J., Sackett, D. D., Arendt, M. F., Yau, S.-L., Bell, C. M. & Mallouk, T. E. Growth and characterization of metal(II) alkanebisphosphonate multilayer thin-films on gold surface. *J. Am. Chem. Soc.* 115, 11855–11862 (1993).
17. Hatzor, A., van der Boom-Moav, T., Yochelis, S., Vaskevich, A., Shanzer, A. & Rubinstein, I. A metal-ion coordinated hybrid multilayer. *Langmuir* 16, 4420–4423 (2000).
18. Umemura, Y., Yamagishi, A. & Tanaka, K.-i. X-ray photoelectron spectroscopic study of alternately layered zirconium and hafnium phosphate thin films on silicon substrates. *Bull. Chem. Soc. Jpn.* 70, 2399–2403 (1997).
19. Beamson, G.; Briggs, D. *High Resolution XPS of organic Polymers*, Wiley, N.Y., 1992.
20. Ogama, T. *J. Vac. Sci. Technol.* 1996, A14, 1309.
21 Larson, P. E.; Kelly, M. A. *J. Vac. Sci. Technol.* 1998, .A16, 3483.
22. Barr, T. L. in *Practical Surface Analysis* (2$^{nd}$ Ed.), Vol. 1,Briggs, D.; Seah M. P. (Eds.), Wiley, N.Y., 1990,p. 357.
23. Tielsch, B. J.; Fulghum, J. E. *Surf. Interf. Anal.* 1996, 24, 422.
24. Tielsch, B. J.; Fulghum, J. E.; Surman, D. J. *Surf. Interf. Anal.* 1996, 24, 459.
25. Tielsch, B. J.; Fulghum, J. E. *Surf. Interf. Anal.* 1997, 25, 904.
26. Bandis, C.; Pate, B. B. *Surf. Sci.* 1996, 345, L23.
27. Cazaux, J.; Leheude, P. *J. Electron Spectrosc. Relat. Phenom.* 1992, 59, 49.
28. Clark, D. T.; Dilks, A.; Thomas, H. R.; Shuttleworth, D. *J. Polym. Sci. Polym. Chem. Ed.* 1979, 17, 627.
29. Beamson, G.; Bunn, A; Briggs, D. *Surf. Interf. Anal.* 1991, 17, 105.
30. Hiraki, A. *Surf. Sci.* 1986, 168, 74.
31. Cros, A.; Dallaporta, H.; Oberlin, J. C. *Appl. Surf. Sci.* 1992, 56–58, 434.
32. Ron, H.; Matlis, S.; Rubinstein, I. *Langmuir* 1998, 14, 1116.

What is claimed is:

1. A method of examining a sample, comprising:
   performing a first spectroscopic analysis of a surface portion of the sample when the sample surface portion is in a first electrical charge state;
   placing the sample surface portion in a second electrical charge state that is different from the first electrical charge state and performing a second spectroscopic analysis of the surface portion of the sample when the sample surface portion is in the second electrical charge state; and
   comparing the first spectroscopic analysis result with the second spectroscopic analysis result to obtain at least one of structural and electrical information about the sample,
   wherein the first and second electrical charge states are given values that enable information to be obtained about sample structural features having dimensions down to 1 nm.

2. The method according to claim 1, wherein the spectroscopic analyses are performed with X-ray photoelectron spectroscopy (XPS).

3. The method according to claim 1, wherein said placing step comprises supplying an excess negative charge to the surface of the sample surface portion.

4. The method according to claim 3 wherein the excess negative charge is supplied by an electron flood gun.

5. The method according to claim 3 wherein the first electrical charge state is a charge neutral state.

6. The method according to claim 1 wherein the second spectroscopic analysis is performed identically to the first spectroscopic analysis.

7. The method according to claim 1 wherein the sample surface is composed of isolated regions of a first material separated by a second material, the materials being selected for causing the result of the first spectroscopic analysis to differ from the result of the second spectroscopic analysis in a manner to provide information about the distribution of the isolated regions or the sample surface portion.

8. The method according to claim 7 wherein the first material is a dielectric and the second material is electrically conductive.

9. The method according to claim 1 wherein the sample is composed of a plurality of superposed layers and at least one of the layers contains a substance selected for causing the result of the first spectroscopic analysis to differ from the result of the second spectroscopic analysis in a manner to provide information about the position of the at least one of the layers in the plurality of superposed layers.

10. A method of examining a sample, comprising:
    performing a first spectroscopic analysis of a surface portion of the sample when the sample surface portion is in a first electrical charge state;
    placing the sample surface portion in a second electrical charge state that is different from the first electrical charge state and performing a second spectroscopic analysis of the surface portion of the sample when the sample surface portion is in the second electrical charge state; and
    comparing the first spectroscopic analysis result with the second spectroscopic analysis result to obtain at least one of structural and electrical information about the sample,
    wherein each spectroscopic analysis result contains data identifying a characteristic of the spectral response for each of at least two elements contained in the sample, and said step of comparing includes
      determining, for each of the at least two elements contained in the sample, a difference between the first spectroscopic analysis result and the second spectroscopic analysis result and
      correlating the differences determined in the determining step for the at least two elements to provide a quantitative value of a characteristic of the sample, and the first and second electrical charge states are given values that enable information to be obtained about sample structural features having dimensions down to 1 nm.

11. The method according to claim 10, wherein the spectroscopic analyses are performed with X-ray photoelectron spectroscopy (XPS).

12. The method according to claim 10, wherein said placing step comprises supplying an excess negative charge to the surface of the sample surface portion.

13. The method according to claim 12 wherein the excess negative charge is supplied by an electron flood gun.

14. The method according to claim 12 wherein the first electrical charge state is a charge neutral state.

15. The method according to claim 10 wherein the second spectroscopic analysis is performed identically to the first spectroscopic analysis.

16. The method according to claim 10 wherein the sample surface is composed of isolated regions of a first material separated by a second material, the materials being selected for causing the result of the first spectroscopic analysis to differ from the result of the second spectroscopic analysis in a manner to provide information about the distribution of the isolated regions or the sample surface portion.

17. The method according to claim 16 wherein the first material is a dielectric and the second material is electrically conductive.

18. The method according to claim 10 wherein the sample is composed of a plurality of superposed layers and at least one of the layers contains a substance selected for causing the result of the first spectroscopic analysis to differ from the result of the second spectroscopic analysis in a manner to provide information about the position of the at least one of the layers in the plurality of superposed layers.

19. Apparatus for examining a sample, comprising:

a spectroscopic analysis instrument including a component that places a surface portion of the sample in different electrical charge states, for performing a first spectroscopic analysis of a surface portion of the sample when the sample surface portion is in a first electrical charge state and performing a second spectroscopic analysis of the surface portion of the sample when the sample surface portion is in a second electrical charge state different from the first electrical charge state; and an arithmetic unit coupled to said instrument to compare the first spectroscopic analysis result with the second spectroscopic analysis result to obtain at least one of structural and electrical information about the sample, wherein each spectroscopic analysis result contains data identifying a characteristic of the spectral response for each of at least two elements contained in the sample, and the comparison performed by the arithmetic unit includes the steps of determining, for each of the at least two elements contained in the sample, a difference between the first spectroscopic analysis result and the second spectroscopic analysis result and correlating the differences determined in the determining step for the at least two elements to provide a quantitative value of a characteristic of the sample, and the first and second electrical charge states are given values that enable information to be obtained about sample structural features having dimensions down to 1 nm.

20. The apparatus according to claim 19, wherein the instrument is a X-ray photoelectron spectroscopy (XPS) instrument.

21. The apparatus according to claim 19, wherein said component supplies an excess negative charge to the surface of the sample surface portion.

22. The apparatus according to claim 21 wherein said component comprises an electron flood gun.

* * * * *